United States Patent [19]
Miller

[11] Patent Number: 5,523,056
[45] Date of Patent: Jun. 4, 1996

[54] TWIN ROTOR INCUBATOR ASSEMBLY

[75] Inventor: James G. Miller, Hilton, N.Y.

[73] Assignee: Johnson & Johnson Clinical Diagnostics, Inc., Rochester, N.Y.

[21] Appl. No.: 235,041

[22] Filed: Apr. 29, 1994

[51] Int. Cl.[6] .................................................. G01N 35/00
[52] U.S. Cl. .............................. 422/64; 422/63; 422/104; 436/43; 436/46; 436/48
[58] Field of Search .............................. 422/63, 64, 65, 422/99, 104; 435/809; 436/43, 44, 45, 46, 48

[56] References Cited

U.S. PATENT DOCUMENTS

| | | | |
|---|---|---|---|
| 3,912,452 | 10/1975 | Sodickson et al. | 422/64 |
| 4,296,069 | 10/1981 | Smith et al. | 422/64 |
| 4,298,571 | 11/1981 | DiFulvio et al. | 422/64 |
| 4,512,952 | 4/1985 | Blanding et al. | |
| 4,568,519 | 2/1986 | Hamilton et al. | 422/64 |
| 4,774,055 | 9/1988 | Wakatake et al. | 422/64 |
| 4,963,333 | 10/1990 | Shaw et al. | 422/99 |
| 5,034,191 | 7/1991 | Porte | 422/64 |
| 5,051,238 | 9/1991 | Umetsu et al. | 422/64 |
| 5,073,342 | 12/1991 | Porte et al. | 422/64 |
| 5,075,079 | 12/1991 | Kerr et al. | 422/64 |
| 5,106,586 | 4/1992 | Muszak et al. | |
| 5,196,168 | 3/1993 | Muszak et al. | 422/64 |
| 5,229,074 | 7/1993 | Heath et al. | 422/64 |

*Primary Examiner*—James C. Housel
*Assistant Examiner*—Long V. Le
*Attorney, Agent, or Firm*—Dana M. Schmidt

[57] ABSTRACT

An incubator assembly useful in a clinical analyzer having at least two incubators, each having a rotationally driven rotor assembly having a plurality of slide element holding stations, which incubators are stacked one above the other to define a substantially vertical arrangement. In a preferred embodiment, in which the incubators are of varying size, the smaller rotor assembly is horizontally offset so that the outside diameter of each rotor assembly is coincident in one location, preferably an input station, so that slide elements can be loaded into and removed more conveniently from either rotor assembly.

5 Claims, 8 Drawing Sheets

5,523,056

TWIN ROTOR INCUBATOR ASSEMBLY

FIELD OF THE INVENTION

The invention is directed to the field of clinical diagnostic analyzers, and in particular to an improved incubator.

BACKGROUND OF THE INVENTION

In the field of clinical analyzers, it is not uncommon for there to be provided a plurality of incubators within the confines of a specific mainframe. Usually this is done to either enhance throughput or to allow each incubator to be dedicated to a particular type of assay, e.g., potentiometric instead of colorimetric. Examples are shown in, e.g., U.S. Pat. No. 4,296,069.

Such analyzers typically position the plural incubators side-by-side. Although this has worked well in most instances, it does tend to require a machine footprint of substantial area, since the path of the test element, for example, a slide element, is more or less two-dimensional, that is, in the horizontal plane.

Therefore, prior to this invention there has been a need to provide for an analyzer having plural incubators but without requiring such a substantial footprint or horizontal lay-out.

RELATED APPLICATIONS

The concept of raising and lowering a cover of a stacked incubator assembly is disclosed and claimed in commonly-owned and co-filed U.S. application Ser. No. 08/236,909, entitled RAISING MECHANISM FOR INCUBATOR COVER, by James G. Miller and Gary S. Hartman [Doc 68845].

The concept of providing an elevator to allow slide elements to be loaded and unloaded at a single station for a stacked incubator assembly is disclosed and claimed in commonly owned and co-filed U.S. application Ser. No. 08/236,908, entitled Analyzer Elevator Assembly, by Martin Muszak, Alexander Hirsch and Michael LaCourt [Doc 66608], now U.S. Pat. No. 5,419,871.

SUMMARY OF THE INVENTION

The present invention solves the above stated needs by providing an incubator assembly for use in a chemical analyzer, the assembly having a plurality of stations circumferentially disposed for holding a slide test element in a rotor assembly, the rotor assembly being rotatably movable about a rotational axis and having at least one loading and unloading station, characterized in that:

the incubator assembly comprises at least two incubators, each including a rotor assembly wherein a first rotor assembly of one incubator is positioned above the other rotor assembly of the at least one other incubator.

An advantageous feature of the present invention is that providing an incubator assembly as described reduces the effective footprint area required for a mainframe analyzer. The present invention provides a savings in space without reducing the effective throughput of a clinical analyzer. Furthermore, the reduced size requirements of an analyzer having an incubator assembly as described allows an analyzer to be built more cheaply, and also allows the capability of a typical footprint to be increased significantly.

Other advantageous features will become apparent upon reference to the following Description of the Preferred Embodiments, when read in light of the attached drawings.

DETAILED DESCRIPTION OF THE PREFERRED EMBODIMENTS

The invention is described hereinafter with respect to a preferred embodiment, in an analyzer that using dried chemistry analytical test elements, and particularly one having a single loading and unloading stations. It should be apparent, however, that the present invention is useful whether or not used as part of a complete mainframe analyzer, whether or not the analytical slide test elements are dried, whether or not the loading and unloading stations are separated or in a single location, and in spite of the types of evaporation caps used to protect the biological fluids contained on a slide element.

In addition, terms such as "above", "up", "down", "lower", "vertical", "horizontal", and "bottom" as used herein refer to a specific orientation for the described embodiment as they are shown in the attached drawings. This specific orientation is provided only as a convenient frame of reference, given that other orientations, such as use in a zero gravity environment, are also possible.

Figure 1:
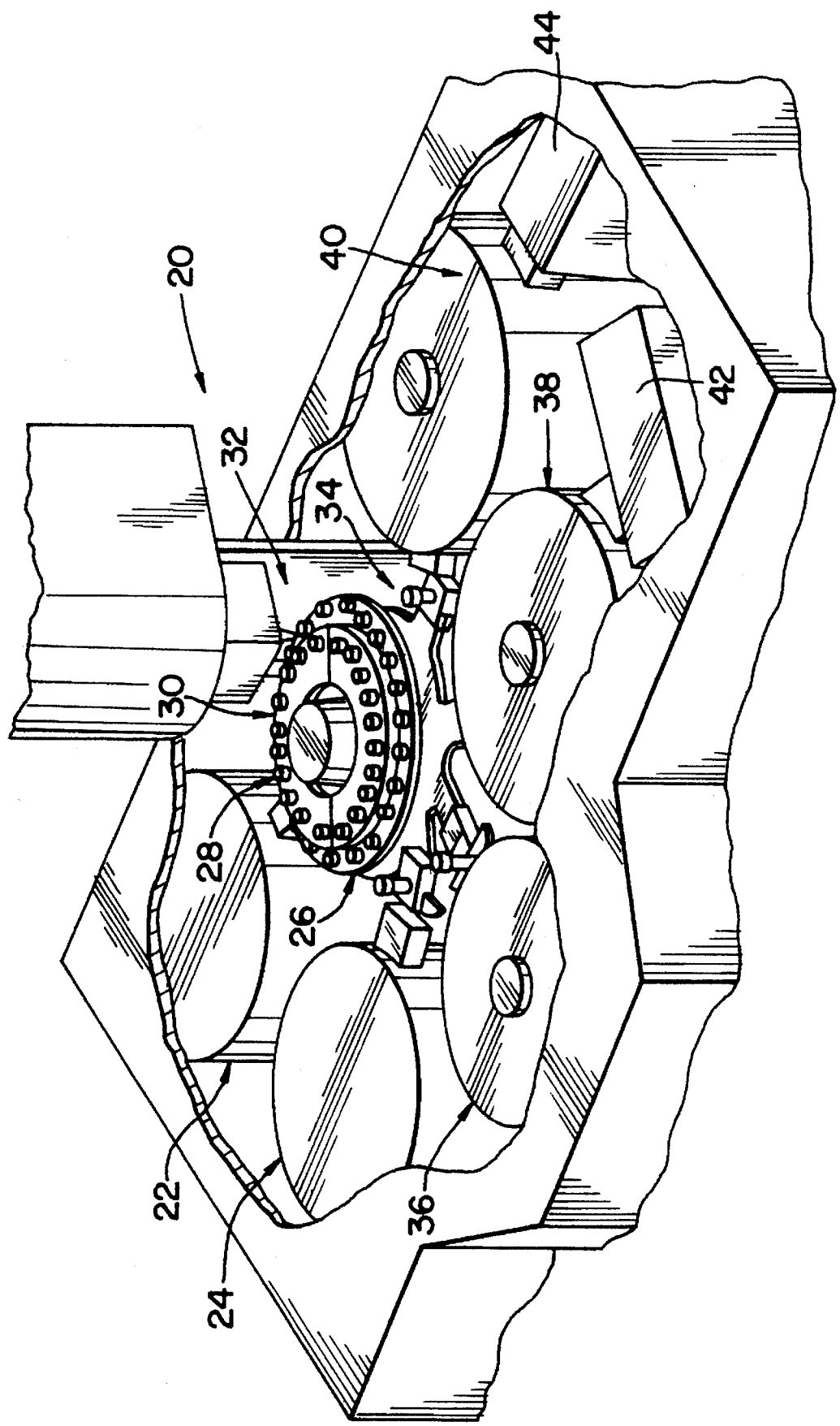
FIG. 1 is a fragmentary isometric view of an analyzer constructed with the incubator of this invention.

Referring to FIG. 1, there is shown a conventional mainframe diagnostic analyzer 20 having one or more supplies of slide test elements at stations 22 and 24, a supply of patient samples 26 and of disposable tips 28 at a rotating station 30, an aspirating and dispensing tower 32 adjacent the station 30, a distributor arm 34 under the station 30 to receive slide test elements to move them to tower 32 and to various incubators, at least three incubators 36, 38, and 40 for incubating slide elements received from the distributor arm 34, and readers 42 and 44 of incubated slide elements optionally disposed to one side of the incubators, all as described in, e.g., U.S. Pat. No. 4,512,952.

Figure 2:
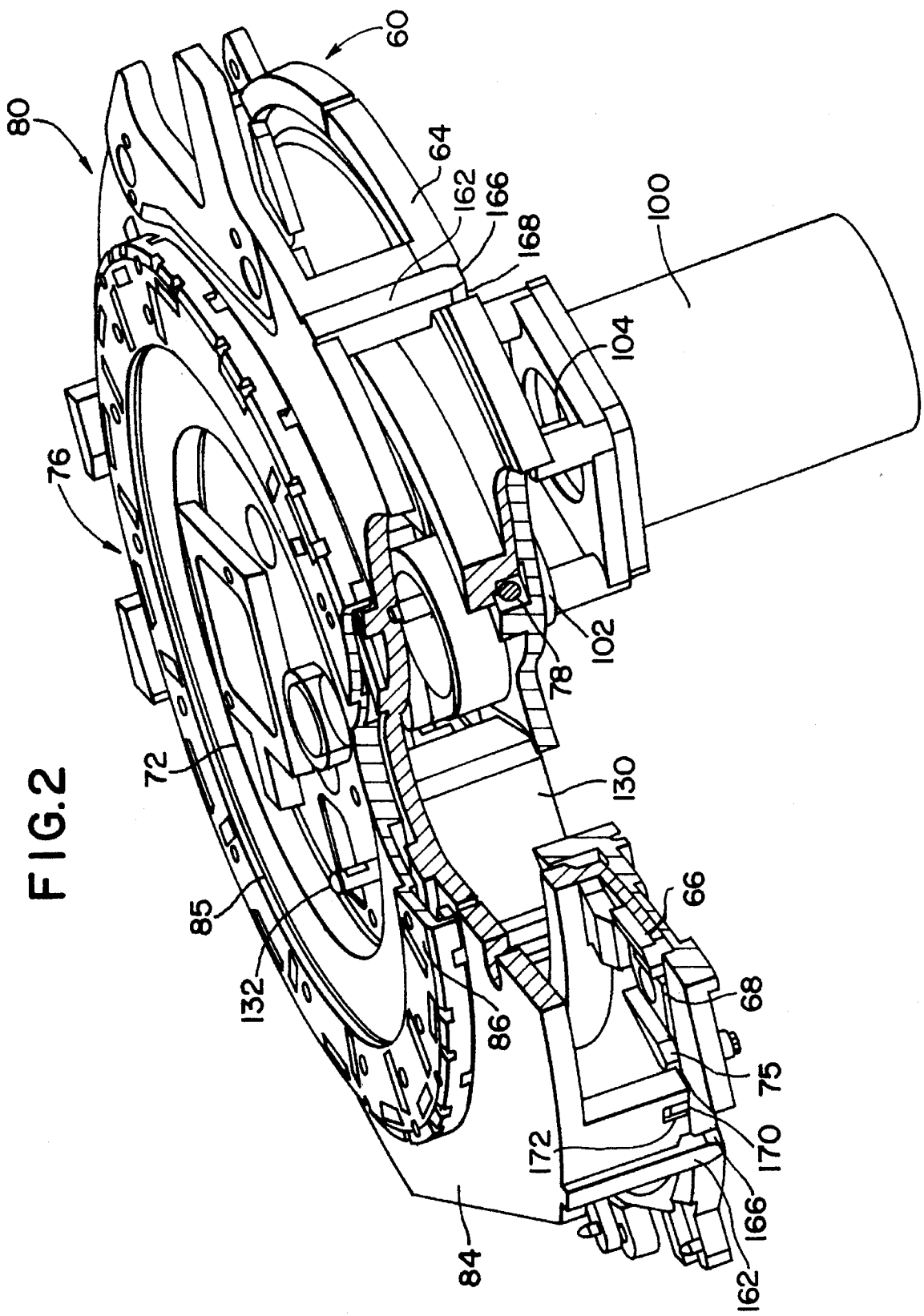
FIG. 2 is a partially cut away isometric view of the upper and lower rotor assemblies for a stacked incubator assembly according to the invention.
Figure 3:
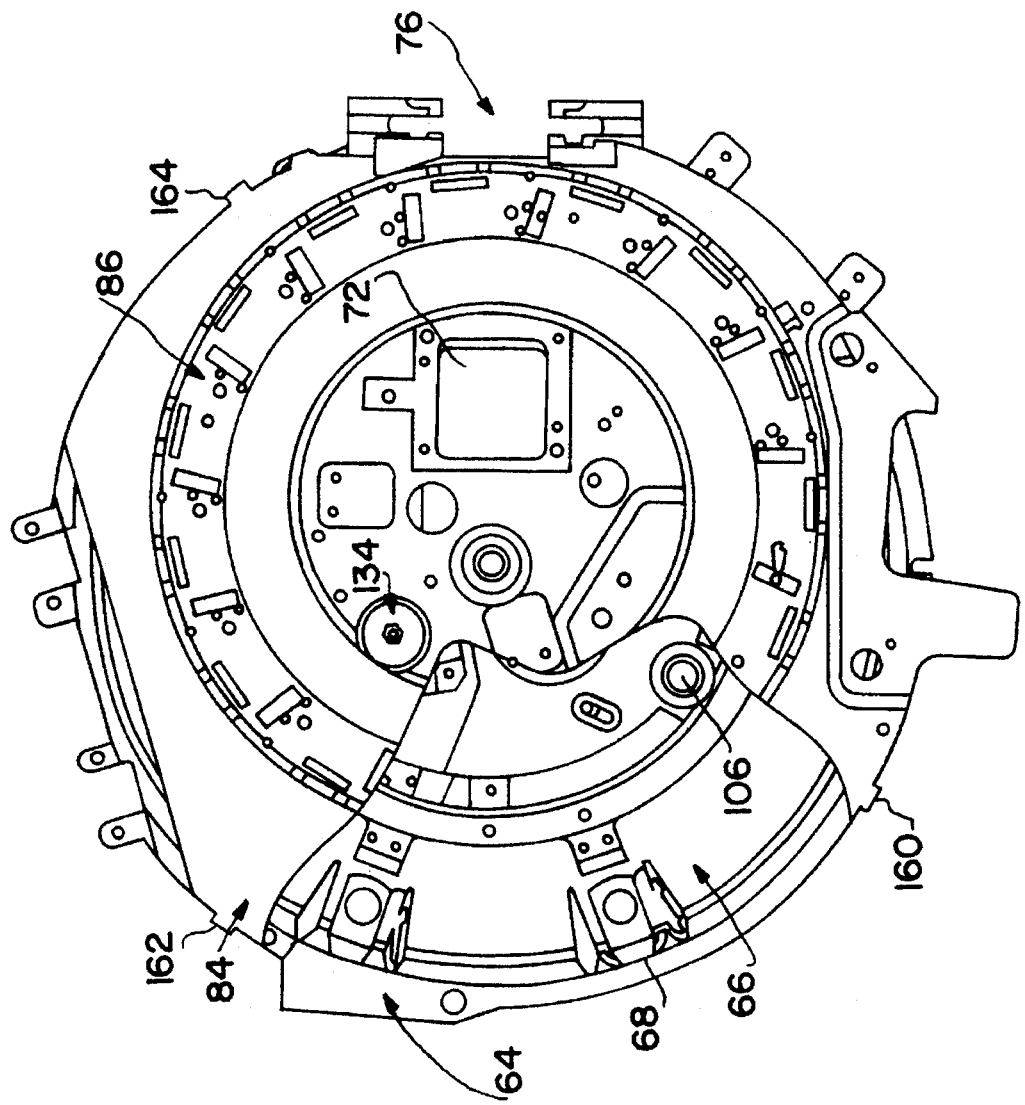
FIG. 3 is a schematic partial plan view of the incubator with the covers omitted.
Figure 4:
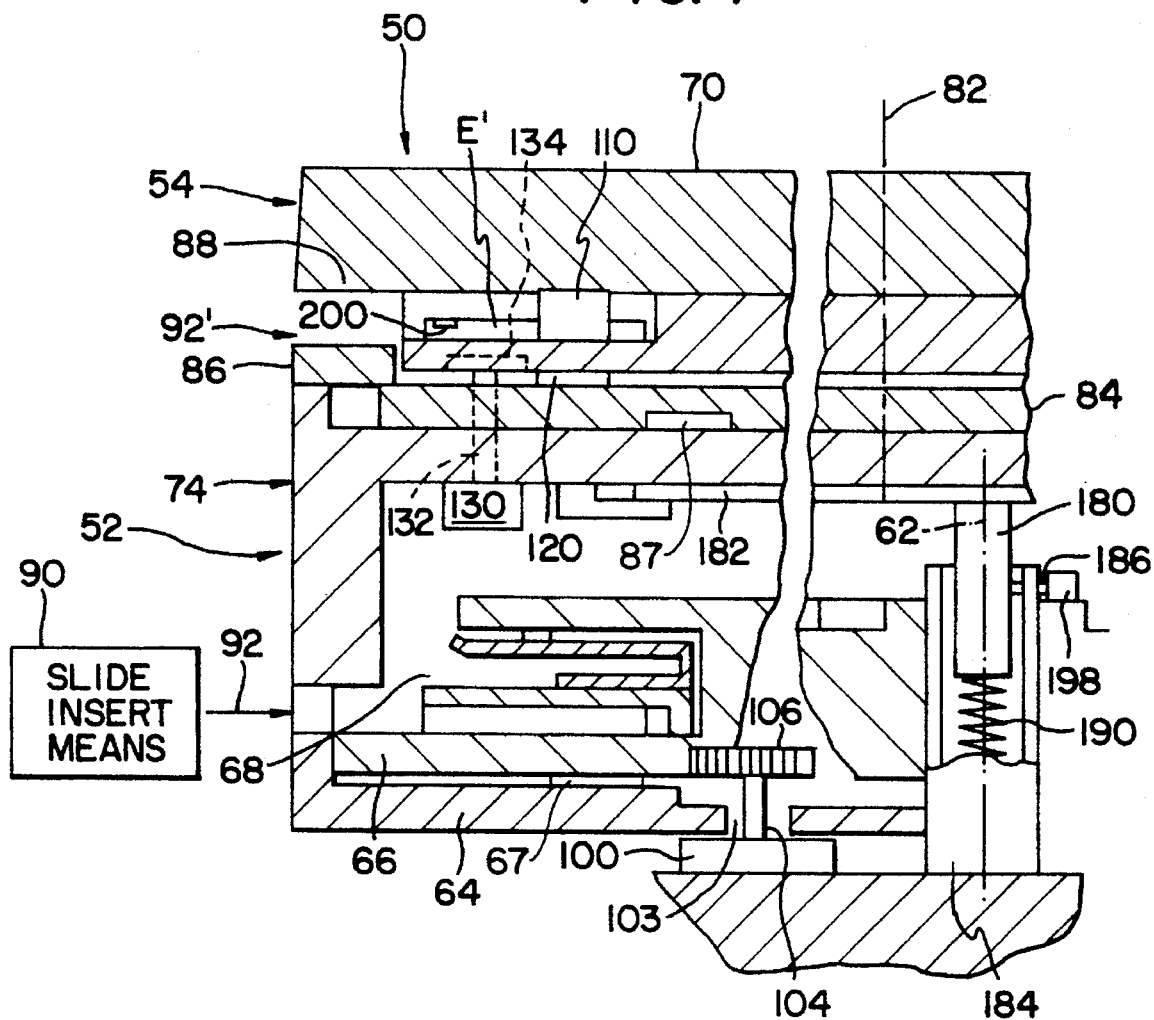
FIG. 4 is a fragmentary partially schematic, elevational view partially in section, of the stacked incubator assembly of the invention with the covers omitted.

Referring now to FIGS. 2, 3 and 4, there is provided an incubator assembly 50, FIG. 4, capable of replacing the incubator 36 and defined by two vertically stacked incubators 52, 54. These incubators are preferably stacked vertically, substantially one above the other as hereinafter described. Each incubator 52, 54, FIG. 4, comprises a rotor assembly which is independently driven as described below about two offset and substantially vertical axes of rotation 62, 82, FIG. 4. In this embodiment, the first and second rotor assemblies 60, 80 are disposed in an orientation in which they are substantially parallel to one another and eccentrically mounted relative to the other, thereby defining the offset rotational vertical axes 62 and 82, FIG. 4.

Each of the rotor assemblies 60, 80 is defined by a rotor 66, 86, having a circular cross section which is mounted for rotation on lower and upper support plates 64, 84, respectively. A series of adjacently and evenly spaced stations 68, 88 are disposed about the circumference of each rotor 66, 86. The upper rotor 84 according to this embodiment is slightly smaller than the lower rotor 64. As a result, when viewed from above, FIG. 3, the footprint of the upper incubator falls substantially within the footprint of the lower incubator.

A input or "home" station 76 is provided for the loading of test elements into either rotor assembly. An exit chute 72 is also adjacently positioned relative to the home station 76 for disposing of elements which have completed testing, the details of which are commonly known in the field.

Figure 5:
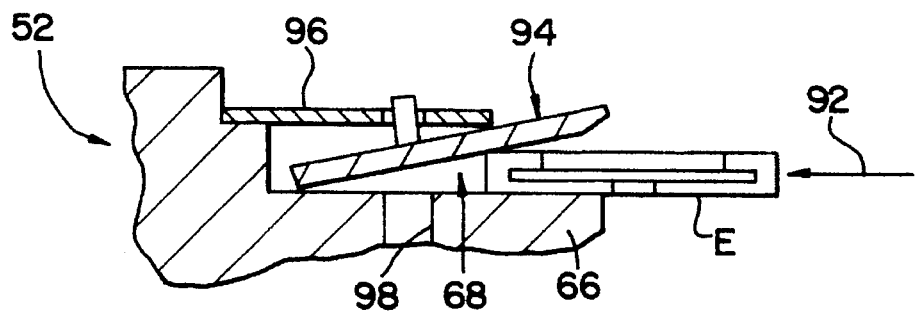
FIG. 5 is a fragmentary elevational view in section showing details of a lower incubator station.

Referring now to FIGS. 2, 4 and 5, the lower incubator 52 is described in more detail. This incubator is preferably used for colorimetric-type test elements of the type available from Eastman Kodak Company under the trademark "EKTACHEM". Such elements produce a detectable color change. Incubator 52 is conventional and is preferably dedicated to rate type assays. It comprises, as shown in U.S. Pat. No. 5,106,586, among others, a rotor 66 that receives at stations 68, a slide test element E from any slide element insert means 90 that moves the slide element in the direction of arrow 92. An evaporation cap 94, used to keep sample contained on test element E from prematurely evaporating, is spring-biased by a spring 96, down onto the slide element. Spring 96 can be flat, as shown, or a J-spring as in the '586 patent. The element E can be read by a reader (not shown) located below the rotor 66 that illuminates element E through an aperture 98. The lower rotor 66, according to this embodiment, can have up to 27 stations disposed about its periphery, though FIG. 2 shows a fewer number number of stations for clarity. Each station 68, FIG. 2, is actually a slotted region having a pair of guiding shoulders 75, FIG. 2, to retain the element therein as it is biased by the spring 96.

The lower rotor 66 is mounted for rotation about vertical axis 62 to the lower support plate 64. A motor 100, having an output shaft 104 extending through an aperture 103 in the lower support plate 64 is connected in a manner conventionally known to a drive pinion gear 106. When the motor 100 is powered, the output shaft 104 rotates along with the pinion gear 106 which engages a toothed inner periphery (not shown) of the lower rotor 66. A ring bearing 102, FIG. 2, situated in a circumferential slot 78, FIG. 2, located between the lower support plate 64 and the rotor 64 allows relatively free rotation of the rotor.

Figure 6:
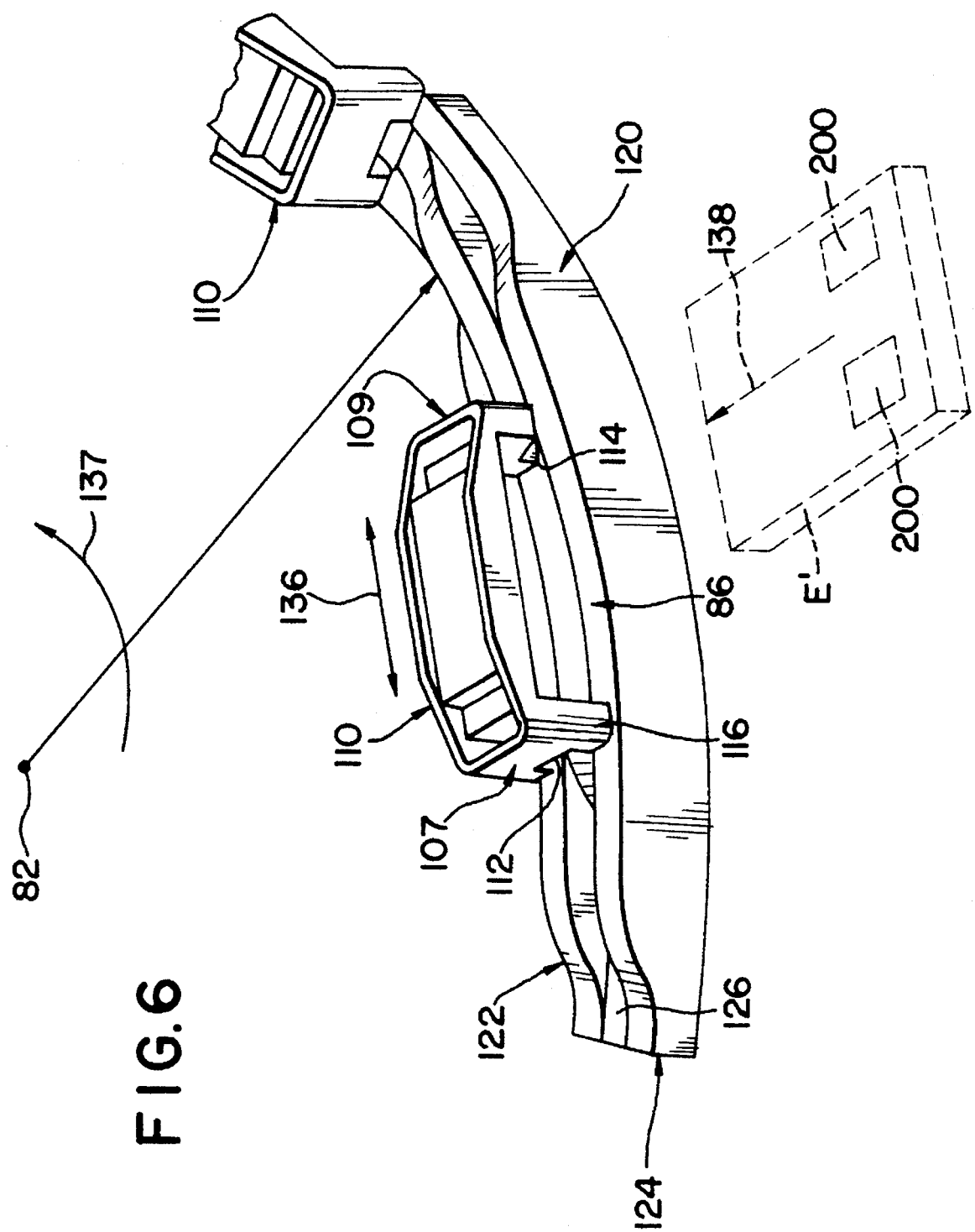
FIG. 6 is a fragmentary isometric view of the upper incubator of the stacked incubator assembly.

Turning now to FIG. 6, a discussion of the upper incubator 54 follows. This incubator is preferably dedicated to potentiometric-type slide test elements, such as those available from Eastman Kodak Company under the tradename of "EKTACHEM". A preferred construction of such an incubator 54 is that disclosed and claimed in commonly owned U.S. Ser. No. 056,637 filed on May 3, 1993 by James G. Miller and entitled "Improved Cap Raising Mechanism for an Incubator". More specifically, the upper incubator 54 comprises a rotor assembly 80 having a number of stations 88 which are evenly spaced about the circumference of rotor 86, each of which is capable of receiving a potentiometric slide element E', covered by an evaporator cap 110 having legs 112, 114, 116 that project through the rotor 86 (omitted in the FIG. 6) to a stationary cam track 120 which is positioned beneath. Track 120 has a plurality of rails 122, 124, 126 each designed to act on one of the three legs 112, 114, 116 so that the cap 110 raises and lowers in a uniform fashion, without any significant sideways thrust (arrow 136 is a force less than 1G) caused by one side of the cap 109 coming down before the other side 107. That is, the raised portion of the rail 126 is offset from the raised portions of the rails 122, 124 exactly the distance between leg 112 and leg 114. As the rotor 86 is rotated, per arrow 137, cap 110 thus goes up to allow a slide element E' to be inserted, into a station 86, and then down to cover the liquid-bearing part 200, without a sideways jarring of the element.

Rotation of the upper rotor 86 about the vertical axis 82, per arrow 137, is achieved in a similar fashion as that of the lower rotor 64; that is by a motor 130 having an output shaft 132 for driving an attached pinion gear 134 which engages the inner toothed periphery 85 of the rotor. Rotor 84 is mounted for rotation to the upper support plate 84 by means of a continuous ring bearing (not shown), which is introduced into a slot (not shown) provided in the upper support plate. Alternatively, a plurality of bearing shoes (not shown) can be placed in the slot in lieu of a continuous ring bearing to allow rotation of the upper rotor 86 about the axis 82.

Elements E' can be loaded onto the rotor 82, and specifically at stations 88, as shown in phantom per arrow 138 by the same slide insert means 90 as is used by the lower incubator 52, see FIG. 4, or by a slide distributor 34, FIG. 1. A potentiometric read station (not shown), features a pair of electrodes (not shown) that are raised and lowered into contact with the liquid bearing portions 200 of the element E'. This station is not activated until an ISE test element E' is positioned thereunder, ready for reading, as determined and controlled by a suitable microprocessor, as is conventionally known.

Upper rotor 86 is smaller in diameter than the lower rotor 66 and is sized to fit up to 15 slide elements E'. Because of the disparity in size between the two rotors, the respective vertical axes of rotation 62, 82 are horizontally offset from each other, as shown schematically in FIG. 2, in order to provide a minimal offset at the "home" position 76. At position 76, as shown in the sectional view of FIG. 2, it can be seen that outside diameters of the two rotor assemblies 60, 80 are literally coincident. In the present embodiment, an offsetting of axis 82 by about 0.866 inches horizontally from axis 62 provides this coincidence, allowing slide elements to be loaded and unloaded more efficiently and conveniently. Hence, the preferred loading and unloading stations are at 92 and 92', FIG. 4. It can be seen that other differently sized rotors can be similarly offset to provide an efficient loading and unloading station.

Referring back to FIG. 2, the upper support plate 84 has three equally spaced legs 160, 162, and 164, (shown only in FIG. 3), located on exterior portions which downwardly depend for engaging the lower support plate 64. Each of the legs 160, 162, 164 have a beveled guiding end portion 166, appropriately sized to fit within a corresponding defined slot 168 in the lower support plate 64. The engagement of the legs 160, 162, 164 into the three slots 168 acts to locate the upper and the lower support plates 84, 64 relative to each other. In addition, two contact surfaces are provided on the lower support plate 64, (of which only one is shown in the FIG.), having upwardly extending engagement pins 170 for mating with a corresponding hole (not shown) and slot 172 which are provided along adjacent legs 164 and 162, respectively, to allow repeatable alignment of the rotor assemblies

60, 80. This engagement also provides the spacing between the upper and lower incubators 52, 54, FIG. 4. In this embodiment, the spacing between the upper and lower support plates is approximately 1 inch, though this value can be easily varied.

Each of the support surfaces are provided with heating elements, such as heating tapes (shown schematically as 67, 87, FIG. 4) which are positioned on the undersurface of the rotors. The plates 64, 84, being made from a material having a high thermal conductivity, such as aluminum are placed in sufficient contact with the rotors 66, 86 for convective heating to occur, as is conventionally known.

Figure 8:
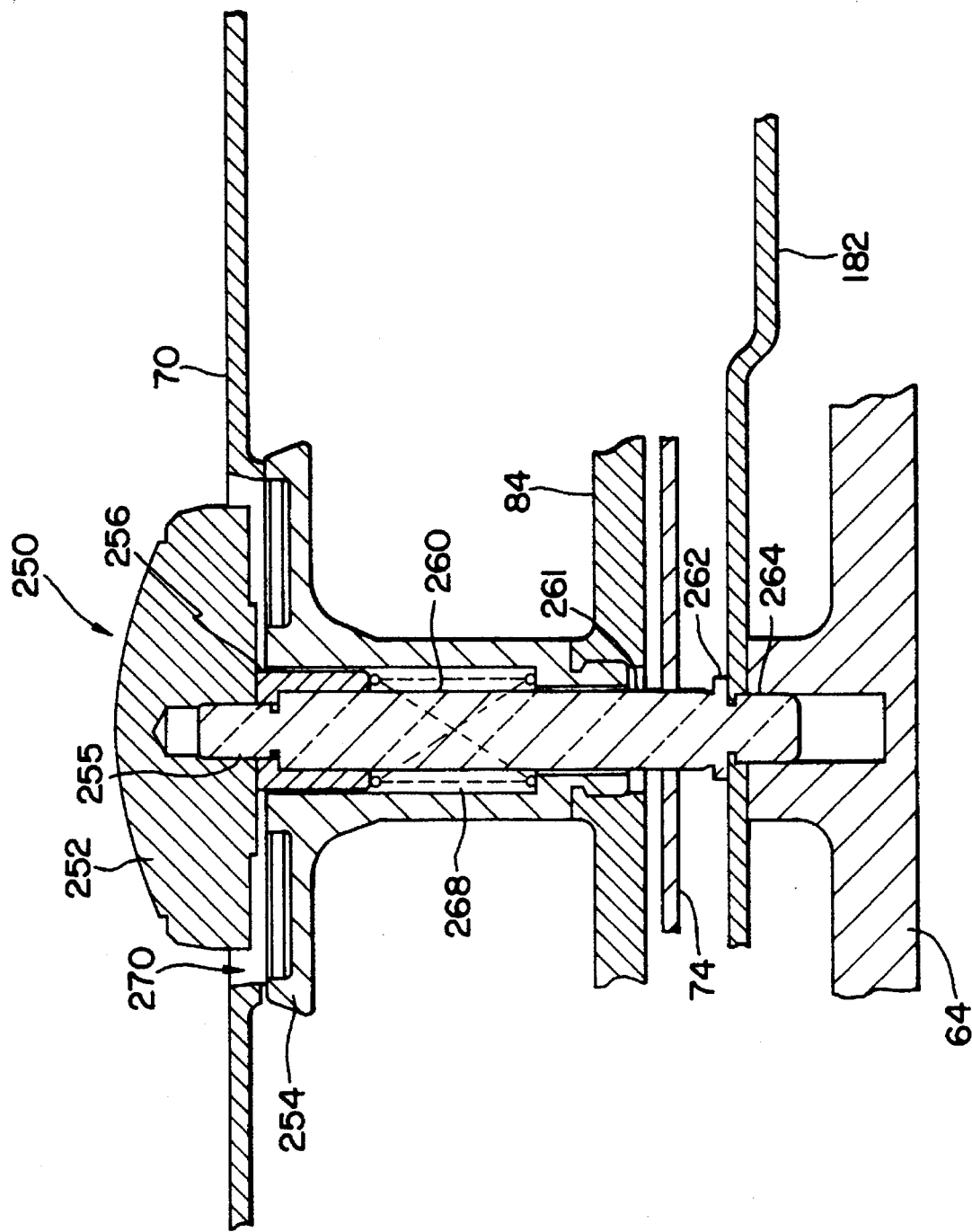
FIG. 8 is a partial side elevational view in section of a lockdown assembly of the top cover which interfaces with the lower cover and the raising mechanism of FIG. 7.
Figure 9:
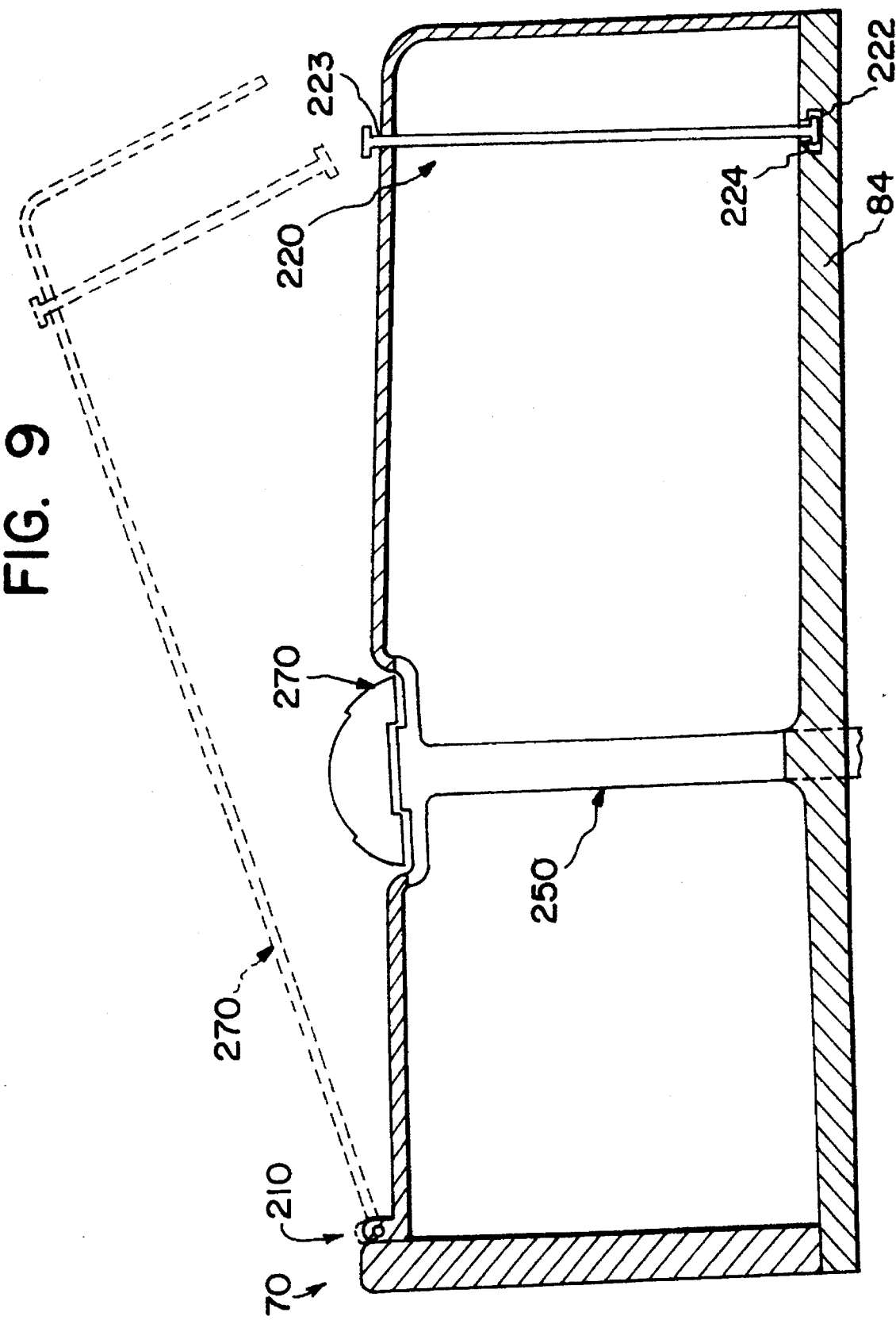
FIG. 9 is a sectional view of the top cover illustrating a latch mechanism for separately opening the cover.

Covers are provided to cover each of the stacked rotor assemblies 60, 80 so as to provide independent thermally controlled chambers. A lower cover 74, FIGS. 7, 8, is provided to cover the lower incubator 52, while a top cover 70, FIGS. 8, 9, is introduced to cover the upper incubator 54.

Conventional type covers which utilize hinged type mechanisms which allow the cover to open are not practicable for the lower cover 74 due to the stacked configuration. To obtain access to the lower incubator 54, the lower cover 74 has to be moved out of the way. Mounting means are now described, by reference to FIG. 7, which allows the lower cover 74 to be pivoted in a horizontal plane without disconnecting the cover from the site of the two incubators 52, 54, FIG. 4.

The mounting means, as more completely described in copending and commonly assigned U.S. application Ser. No. 08/236,909, entitled Raising Mechanism for Incubator Cover by James G. Miller and Gary S. Hartman [Doc. 68845], cross referenced above, comprises a connector comprising a vertical shaft 180 fixed to a lift and turn plate 182, the shaft being slideable through a fixed hollow tube 184 extending from the shaft 180.

Figure 7:
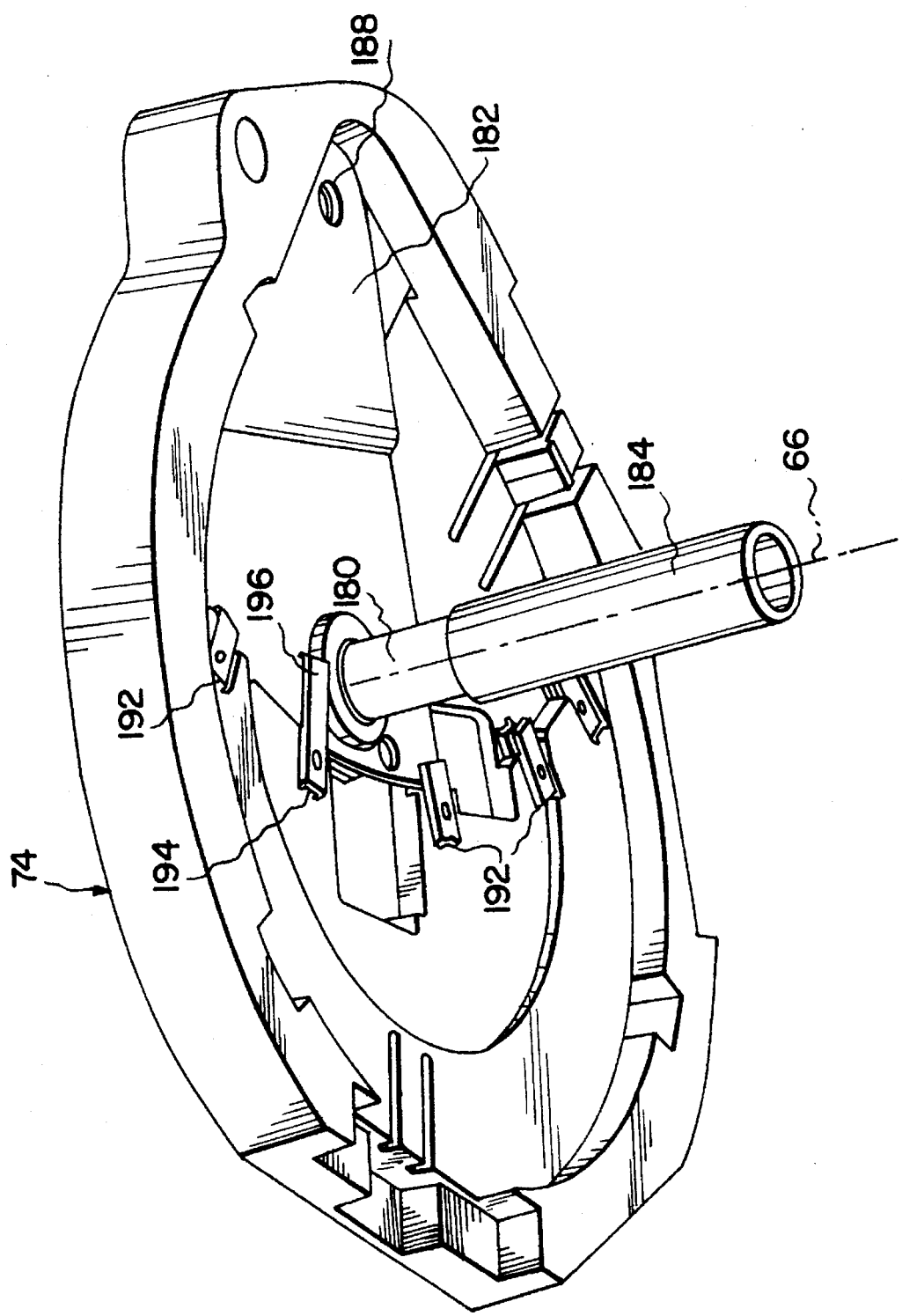
FIG. 7 is an isometric view of the lower cover of the stacked incubator assembly and of a mechanism for the raising of the cover to allow access to the lower incubator.

Still referring to FIG. 7 and offset from axis 66 is a pivot aperture 188 in which a pivot pin (not shown) is inserted. The lower cover 74 is then secured to the lift and turn plate 182, using C-shaped guides 192 and 194 fixed to the undersurface of the plate 182. The notches cut into guides 192 and 194 mate with the curved exterior edge of the lift and turn plate 182. In addition, guide 194 has a camming portion 196 which can swing into contact with a cam follower (not shown) to pivot the lower cover 74 horizontally through an angle in order to access lower incubator 52, FIG. 4, wherein rotation is achieved about the pivot pin.

The shaft 180 is limited to a vertical motion within the tube 184 by a guide pin 186, FIG. 2, which is secured a stationary portion 198 of the incubator which also secures the hollow tube in place. The guide pin 186 penetrates a through hole in the tube 184 and rides within a slot (not shown) cut into the side of the shaft 180, FIG. 2.

Because the upper incubator 52, FIG. 4, is rotated along with the lower cover 74, a compression spring 190, FIG. 2, is mounted between the shaft 180 and a stationary portion 192, FIG. 2, of the incubator assembly. The spring constant of the compression spring 190 is selected so that when the lower cover 74 is completely lowered, FIGS. 4 and 8, it exerts a force about equal to the weight of the lower cover, as well as the upper incubator, FIG. 4. Additional details of the raising cover assembly are provided in the raising mechanism Application cross-referenced previously.

Referring now to FIG. 8, and to hold the lower cover 74 down during usage of the incubators 52, 54, a lockdown assembly 250 is screwed through that cover into the lower incubator plate 64, FIG. 4. The lockdown assembly 250 is engaged through the center of the upper incubator assembly and plate 84, FIG. 4, and comprises a rotatable knob 252 which is seated to a knob tower 254 having an engagement aperture 255 sized to fit a collar 256. The fitted collar 256 engages with one end of an inserted member 260 which is positioned upwardly through a central through opening 261 in the knob tower 254. The inserted member 260 has a flange 262, which is sized larger than the opening 261 in the knob tower 254 to restrict further upward movement when inserted into the opening, as well as an adjacent threaded bottom portion 264 at the other end of the inserted member. The threaded bottom portion 264 is fitted into engagement holes provided in the lift and turn plate 182 and the lower support plate 64, as shown. The opening 261 in the knob tower 254 is adequately sized to fit the inserted member 260, having a recessed portion sized to additionally accommodate a compression spring 268 as well as the collar 256.

When fully assembled according to FIG. 8, the collar 256 bears against the spring 268 to provide a biasing force to allow threading of the bottom portion 264 of inserted member 260 so as to engage the lift and turn plate 182 and the lower support plate 64. In so doing, a locked position is achieved which overcomes the spring force provided by the lower cover raising assembly.

Because the lockdown assembly 250 is accessible from the top of the incubator assembly 50, FIG. 4, the rotatable knob 252 extends above the top cover 70. The top cover 70, however, can be separately removed without having to engage or otherwise disrupt the lower cover raising mechanism. Referring to FIG. 8 and specifically to FIG. 9, it can be seen that the top cover 70 is somewhat conventional having a hinged portion 210 on one side of the cover and a latch mechanism 220 which is disposed at the outer periphery at the other side of the cover. The latch mechanism 220 consists of a single locking pin or fastener 222 which engages corresponding apertures 223, 224 located in the top cover 70 and the upper support plate 84, respectively. A receiving means is provided for locking the fastener 222 after its insertion into the aperture 224. In this embodiment, a ¼ turn fastener is used as are commonly known. In addition, the top cover 70 has a central aperture 270 sized to allow the cover to be raised separately about the hinged portion 210, as shown in phantom in FIG.. 9, without interfering with the lockdown assembly 250. In use, a one quarter turn of the locking fastener 222 engages or disengages the fastener from the upper support plate 84 to allow the top cover 70 to be separately locked or raised as shown.

In operation, and referring in general to the FIGS., the incubator assembly 50 is disposed within an analyzer 20, such as the one shown in FIG. 1, for example, those manufactured by Eastman Kodak Company under the tradename of EKTACHEM.

Each of the slide elements E and E' can be conveniently loaded and unloaded at the stations 92 and 92' into and out of either of any convenient slide moving means. In a preferred arrangement, an elevator (not shown) can be positioned adjacent the lower or upper rotor assemblies 60, 80. The elevator which mounts to attachment detail (not shown) provided on the incubator assembly 50 at home station 78 is described in greater detail in commonly assigned and concurrently filed U.S. application Ser. No. 08/236,908, entitled Analyzer Elevator Assembly, by Martin Muszak, Michael LaCourt and Alexander Hirsch [Docket 66608], co-filed herewith.

It should be apparent from the preceding discussion that the incubator assembly of the present invention can have multiple incubators arranged other than that described. For example, a plurality of incubators could be vertically arranged from one another in either a stacked, a staggered or other configuration.

The invention has been described in detail with particular reference to preferred embodiments thereof, but it will be understood that variations and modifications can be effected within the scope of the invention.

What is claimed is:

1. In an incubator assembly for use in a clinical analyzer that assays for analytes and having a plurality of stations circumferentially disposed for holding a slide test element in a rotor assembly while a reaction occurs therein responsive to said analyte, said rotor assembly being rotatably movable about a rotational axis and having at least one loading and unloading station, the improvement wherein said incubator assembly comprises at least two incubators each having a rotor assembly and means for heating each said rotor assembly, and wherein the rotor assembly of a first incubator is positioned above the rotor assembly of the other of said at least two incubators, and wherein each said rotor assembly includes an axis of rotation and an exterior diameter wherein said first rotor assembly diameter is smaller than said second rotor assembly diameter and is offset from said second rotor assembly such that said rotors are approximately vertically aligned along at least a portion of their respective peripheries to allow loading and unloading in one substantially vertical plane having a minimal offset, by an element input means provided at said loading and unloading stations.

2. An incubator assembly as recited in claim 1, wherein the rotational axis of said first rotor assembly is linearly offset from said second rotor assembly.

3. An incubator assembly as recited in claim 1, further comprising first and second drive means connected to said first and said second rotor assemblies for independently rotating each said rotor assembly about said rotational axis.

4. An incubator assembly as recited in claim 1, wherein each said circumferentially disposed station on each said rotor assembly includes means defining an opening sized to receive said test element.

5. An incubator assembly as recited in claim 1, further comprising evaporation covers positioned along the periphery of either of said rotor assemblies and means for raising and lowering said covers on at least one of said rotor assemblies.

* * * * *